(12) United States Patent
Papen

(10) Patent No.: US 6,521,187 B1
(45) Date of Patent: Feb. 18, 2003

(54) DISPENSING LIQUID DROPS ONTO POROUS BRITTLE SUBSTRATES

(75) Inventor: Roeland F. Papen, Guilford, CT (US)

(73) Assignee: Packard Instrument Company, Downers Grove, IL (US)

( * ) Notice: Subject to any disclaimer, the term of this patent is extended or adjusted under 35 U.S.C. 154(b) by 0 days.

(21) Appl. No.: 09/489,261

(22) Filed: Jan. 21, 2000

Related U.S. Application Data

(63) Continuation-in-part of application No. 09/056,233, filed on Apr. 7, 1998, now Pat. No. 6,203,759, which is a continuation-in-part of application No. 08/656,455, filed on May 31, 1996, now abandoned.
(60) Provisional application No. 60/041,861, filed on Apr. 8, 1997, and provisional application No. 60/067,665, filed on Dec. 5, 1997.

(51) Int. Cl.⁷ ................................................. B01L 3/02
(52) U.S. Cl. ................. 422/100; 73/863.01; 73/863.02; 222/263; 222/333; 222/309; 222/406; 422/99; 436/180
(58) Field of Search ............... 422/99, 100; 436/180; 73/863.01, 863.02; 222/55, 63, 64, 333, 263, 335, 339, 406

(56) References Cited

U.S. PATENT DOCUMENTS

| | | |
|---|---|---|
| 3,427,480 A | 2/1969 | Robinson |
| 3,452,360 A | 6/1969 | Williamson |
| 3,507,269 A | 4/1970 | Berry |
| 3,512,173 A | 5/1970 | Darmouth |
| 3,549,328 A | 12/1970 | Kilburn |
| 3,666,421 A | 5/1972 | Price |
| 3,683,212 A | 8/1972 | Zoltan |
| 3,711,252 A | 1/1973 | Roy |
| 3,798,961 A | 3/1974 | Flambard et al. |
| 3,831,845 A | 8/1974 | Packt |
| 3,832,579 A | 8/1974 | Arndt |
| 3,838,012 A | 9/1974 | Higgens |
| 3,859,169 A | 1/1975 | O'Driscoll et al. |
| 3,902,083 A | 8/1975 | Zoltan |

(List continued on next page.)

FOREIGN PATENT DOCUMENTS

| | | |
|---|---|---|
| DE | 3 007 189 | 11/1980 |
| DE | 3 014 256 | 12/1980 |
| DE | 3 332 491 | 3/1985 |
| DE | 3 833 586 | 7/1989 |
| DE | 3 915 920 | 11/1990 |
| DE | 4 140 533 | 6/1993 |

(List continued on next page.)

OTHER PUBLICATIONS

J.M. Köhler et al., "Micromechanical elements for detection of molecules and molecular design", pp. 202–208, Microsystem Technologies, Springer–Verlag 1995.
Ashley et al. "Development and Characterization of Ink for an Electrostatic Ink Jet Printer" pp. 69–74, IBM J. Res. Develop. (Undated).
Beach et al., "Materials Selection for an Ink Jet Printer" pp. 75–86, IBM J. Res. Develop. (Undated).

(List continued on next page.)

*Primary Examiner*—John Kim
(74) *Attorney, Agent, or Firm*—Jenkens & Gilchrist

(57) ABSTRACT

A system for aspirating and ejecting microvolume drops of liquid onto porous sites of a substrate wafer is presented. The system includes a microdispenser employing a piezoelectric transducer attached to a glass capillary, a means for priming and aspirating transfer liquid into the microdispenser, for controlling the pressure of the system liquid, and for washing the microdispenser between liquid transfers, and a pressure sensor to measure the system liquid pressure and produce a corresponding electrical signal. The drops are generally in the 10 to 100 micron range and the pores are generally 10 to 10,000 times smaller than the diameter of the drops deposited thereon. The resulting spots are uniform, and only slightly larger in diameter than that of the drops. The drops are ejected from a distance greater than the diameter of the drops, thus avoiding any contact with the dispenser that could damage the wafer.

8 Claims, 7 Drawing Sheets

U.S. PATENT DOCUMENTS

| | | | |
|---|---|---|---|
| 3,946,398 A | 3/1976 | Kyser et al. | |
| 3,958,249 A | 5/1976 | DeMaine et al. | |
| 3,964,871 A | 6/1976 | Hochstasser | |
| 3,975,162 A | 8/1976 | Renn | |
| 3,985,467 A | 10/1976 | Lefferson | |
| 3,994,423 A | 11/1976 | Burg | |
| 3,996,006 A | 12/1976 | Pagano | |
| 4,038,570 A | 7/1977 | Durley, III | |
| 4,046,513 A | 9/1977 | Johnson | |
| 4,084,165 A | 4/1978 | Skafvensted et al. | |
| 4,087,332 A | 5/1978 | Hansen | |
| 4,193,009 A | 3/1980 | Durley, III | |
| 4,216,245 A | 8/1980 | Johnson | |
| 4,223,558 A | 9/1980 | Schmider et al. | |
| 4,234,103 A | 11/1980 | Strobl, Jr. et al. | |
| 4,241,406 A | 12/1980 | Kennedy et al. | |
| 4,278,983 A | 7/1981 | Halasz | |
| 4,293,867 A | 10/1981 | Isayama | |
| 4,298,345 A | 11/1981 | Sodickson et al. | |
| 4,308,546 A | 12/1981 | Halasz | |
| 4,341,310 A | 7/1982 | Sangiovanni et al. | |
| 4,366,490 A | 12/1982 | DeBonte et al. | |
| 4,410,020 A | 10/1983 | Lorenz | 141/65 |
| 4,418,356 A | 11/1983 | Reece | |
| 4,426,031 A | 1/1984 | Halasz | |
| 4,447,375 A | 5/1984 | Schimmelpfennig | |
| 4,492,322 A | 1/1985 | Hieftje et al. | |
| 4,498,088 A | 2/1985 | Kanayama | |
| 4,503,012 A | 3/1985 | Starr | |
| 4,504,845 A | 3/1985 | Kattner et al. | |
| 4,512,722 A | 4/1985 | Mouton | |
| 4,514,743 A | 4/1985 | Roschlein et al. | |
| 4,518,974 A | 5/1985 | Isayama | |
| 4,530,463 A | 7/1985 | Hiniker et al. | |
| 4,539,575 A | 9/1985 | Nilsson | |
| 4,548,825 A | 10/1985 | Voss et al. | |
| 4,550,325 A | 10/1985 | Viola | |
| 4,600,928 A | 7/1986 | Braun et al. | |
| 4,633,413 A | 12/1986 | Bailey et al. | |
| 4,646,104 A | 2/1987 | Braun | |
| 4,651,161 A | 3/1987 | Rich et al. | |
| 4,672,398 A | 6/1987 | Kuwabara et al. | |
| 4,681,741 A | 7/1987 | Hanaway | |
| 4,682,710 A | 7/1987 | Turner, Jr. et al. | |
| 4,691,850 A | 9/1987 | Krischmann et al. | 222/642 |
| 4,695,852 A | 9/1987 | Scardovi | |
| 4,701,754 A | 10/1987 | Provonchee | |
| 4,777,832 A | 10/1988 | Prodosmo et al. | |
| 4,877,745 A | 10/1989 | Hayes et al. | |
| 4,934,419 A | 6/1990 | Lamont et al. | 141/94 |
| 4,976,259 A | 12/1990 | Higson et al. | |
| 5,039,614 A | 8/1991 | Dekmezian et al. | |
| 5,055,263 A | 10/1991 | Meltzer | |
| 5,059,393 A | 10/1991 | Quenin et al. | |
| 5,072,235 A | 12/1991 | Slowik et al. | |
| 5,141,871 A | 8/1992 | Kureshy et al. | |
| 5,225,750 A | 7/1993 | Higuchi et al. | |
| 5,229,679 A | 7/1993 | Higuchi et al. | |
| 5,232,664 A | 8/1993 | Krawzak et al. | |
| 5,252,294 A | 10/1993 | Kroy et al. | 422/101 |
| 5,297,734 A | 3/1994 | Toda | |
| 5,306,510 A | 4/1994 | Meltzer | |
| 5,334,353 A | 8/1994 | Blattner | |
| 5,356,034 A | 10/1994 | Schlumberger | |
| 5,365,783 A | 11/1994 | Zweifel | |
| 5,378,962 A | 1/1995 | Gray et al. | |
| 5,415,679 A | 5/1995 | Wallace | |
| 5,449,345 A | 9/1995 | Taylor et al. | |
| 5,453,091 A | 9/1995 | Taylor et al. | |
| 5,457,527 A | 10/1995 | Manns et al. | |
| 5,485,828 A | 1/1996 | Hauser | |
| 5,525,515 A | 6/1996 | Blattner | 436/49 |
| 5,527,707 A | 6/1996 | Fukazawa | |
| 5,529,754 A | 6/1996 | Bonacina et al. | |
| 5,543,827 A | 8/1996 | VanSteekiste et al. | |
| 5,554,339 A | 9/1996 | Cozzette et al. | |
| 5,620,004 A | 4/1997 | Johansen | |
| 5,630,793 A | 5/1997 | Rowe | |
| 5,651,648 A | 7/1997 | Furey | |
| 5,653,726 A | 8/1997 | Kieturakis | |
| 5,655,446 A | 8/1997 | Watanabe | |
| 5,658,723 A | 8/1997 | Oberhardt et al. | |
| 5,658,802 A | 8/1997 | Hayes et al. | |
| 5,659,173 A | 8/1997 | Putterman et al. | |
| 5,661,245 A | 8/1997 | Svoboda et al. | |
| 5,663,754 A | 9/1997 | Lorenze et al. | |
| 5,673,073 A | 9/1997 | Childers et al. | |
| 5,674,238 A | 10/1997 | Sample et al. | |
| 5,675,367 A | 10/1997 | Scheffelin et al. | |
| 5,681,757 A * | 10/1997 | Hayes | 437/7 |
| 5,682,236 A | 10/1997 | Trolinger | |
| 5,685,310 A | 11/1997 | Porter | |
| 5,685,848 A | 11/1997 | Robinson et al. | |
| 5,690,907 A | 11/1997 | Lanza et al. | |
| 5,691,478 A | 11/1997 | Barry et al. | |
| 5,693,016 A | 12/1997 | Gumaste et al. | |
| 5,694,919 A | 12/1997 | Rubsamen et al. | |
| 5,694,946 A | 12/1997 | Tenerz et al. | |
| 5,695,457 A | 12/1997 | St. Goar et al. | |
| 5,695,461 A | 12/1997 | Schaible | |
| 5,695,468 A | 12/1997 | Lafontaine et al. | |
| 5,695,740 A | 12/1997 | Porter | |
| 5,697,375 A | 12/1997 | Hickey | |
| 5,698,018 A | 12/1997 | Bishop et al. | |
| 5,700,848 A | 12/1997 | Soon-Shiong et al. | |
| 5,701,899 A | 12/1997 | Porter | |
| 5,702,384 A | 12/1997 | Umeyama et al. | |
| 5,763,278 A | 6/1998 | Sickinger et al. | |
| 5,843,767 A | 12/1998 | Beattie | 435/287.1 |
| 5,877,580 A * | 3/1999 | Swierkowski | 310/328 |
| 5,916,524 A | 6/1999 | Tisone | |
| 5,927,547 A | 7/1999 | Papen et al. | |
| 6,015,820 A | 1/2000 | Bisagni et al. | |
| 6,063,339 A | 5/2000 | Tisone et al. | |
| 6,083,762 A | 7/2000 | Papen t al. | |
| 6,203,759 B1 | 3/2001 | Pelc et al. | |
| 6,244,575 B1 * | 6/2001 | Vaartstra et al. | 261/141 |
| 6,280,148 B1 * | 8/2001 | Zengerle et al. | 417/44.1 |

FOREIGN PATENT DOCUMENTS

| | | |
|---|---|---|
| DE | 0 301 771 | 11/1993 |
| DE | 19 532382 | 3/1997 |
| EP | 0 012 821 | 11/1979 |
| EP | 0 024 230 | 2/1981 |
| EP | 0 072 558 | 2/1983 |
| EP | 0 119 573 | 9/1984 |
| EP | 0 169 071 | 1/1986 |
| EP | 0 202 022 | 11/1986 |
| EP | 0 219 177 | 4/1987 |
| EP | 0 268 237 | 5/1988 |
| EP | 0 412 431 | 2/1991 |
| EP | 0 432 992 | 6/1991 |
| EP | 0 433 992 | 6/1991 |
| EP | 0 438 136 | 7/1991 |
| EP | 0 446 972 | 9/1991 |
| EP | 0 508 531 | 10/1992 |
| EP | 0 513 441 | 11/1992 |
| EP | 0 545 284 | 6/1993 |
| EP | 0 548 872 | 6/1993 |
| EP | 0 568 024 | 11/1993 |
| EP | 0 581 708 | 2/1994 |

| | | |
|---|---|---|
| EP | 0 628 413 | 12/1994 |
| EP | 0 655 256 | 5/1995 |
| EP | 0 712 232 | 5/1996 |
| EP | 0 545 284 | 6/1996 |
| EP | 0 718 046 | 6/1996 |
| EP | 0 747 689 | 12/1996 |
| EP | 0 761 256 | 3/1997 |
| EP | 0 763 742 | 3/1997 |
| EP | 0 766 946 | 5/1997 |
| EP | 0 779 436 | 6/1997 |
| EP | 0 799 436 | 6/1997 |
| EP | 0 781 987 | 7/1997 |
| EP | 0 788 809 | 8/1997 |
| EP | 0 789 383 | 8/1997 |
| EP | 0 795 409 | 9/1997 |
| EP | 0 810 096 | 12/1997 |
| EP | 0 810 438 | 12/1997 |
| ES | 2073992 | 8/1995 |
| JP | 55-79167 | 12/1978 |
| JP | 1-038147 | 2/1989 |
| JP | 1-150549 | 6/1989 |
| JP | 01234144 | 9/1989 |
| JP | 2-017079 | 1/1990 |
| RU | SU 0 783 635 | 11/1980 |
| RU | SU 0 791 954 | 12/1980 |
| RU | SU 0 858 845 | 9/1981 |
| RU | SU 1 089 420 | 4/1985 |
| RU | SU 1 262 376 | 10/1986 |
| RU | SU 1 436 057 | 11/1988 |
| RU | SU 1 740 007 | 6/1992 |
| RU | 2011961 | 4/1994 |
| WO | WO 89/00725 | 1/1989 |
| WO | WO 89/10193 | 11/1989 |
| WO | WO 90/11040 | 10/1990 |
| WO | WO 92/11050 | 7/1992 |
| WO | WO 92/15256 | 9/1992 |
| WO | WO 92/15361 | 9/1992 |
| WO | WO 92/18608 | 10/1992 |
| WO | WO 93/10910 | 6/1993 |
| WO | WO 94/06568 | 3/1994 |
| WO | WO 95/01559 | 1/1995 |
| WO | WO 95/04502 | 2/1995 |
| WO | WO 95/26236 | 10/1995 |
| WO | WO 95/35212 | 12/1995 |
| WO | WO 96/12609 | 5/1996 |
| WO | WO 97/16251 | 5/1997 |
| WO | WO 99/28494 | 6/1999 |
| WO | WO 99/36576 | 7/1999 |
| WO | WO 99/53102 | 10/1999 |
| WO | WO 00/09738 | 2/2000 |

OTHER PUBLICATIONS

Boillat et al., "A Differential Pressure Liquid Flow Sensor for Flow Regulation and Dosing Systems," Proceedings IEEE, Micro Electro Mechanical Systems, MEMS, '95 Amsterdam.

Buehner, et al., "Application of Ink Jet Technology to a Word Processing Output Printer", pp. 1–9, IBM J. Res. Develop. (Undated).

Carmichael, "Controlling Print Height in an Ink Jet Printer" pp. 52–55, IBM J. Res. Develop. (Undated).

Curry, Portig, "Scale Model of an Ink Jet", pp. 10–20, IBM J. Res. Develop. (Undated).

Filmore et al. Drop Charging and Deflection in an Electrostatic Ink Jet Printer, pp. 37–47, IBM J. Res. Develop. (Undated).

Holcombe, Eklund & Grice, "Vaporization and Atomization of Large Particles in an Acetylene/Air Flame", pp. 2097–2103, Analytical Chemistry, vol. 50, No. 14, Dec. 1978.

Joshi and Sacks "Circular Slot Burner–Droplet Generator System for High–Temperature Reaction and Vapor Transport Studies" pp. 1781–1785, Analytical Chemistry, vol. 51, No. 11, Sep. 1979.

Lee "Boundary Layer Around a Liquid Jet" pp. 48–51, IBM J. Res. Develop. (Undated).

Levanoni, "Study of Fluid flow through Scaled–up Ink Jet Nozzles" pp. 56–68, IBM J. Res. Develop. (Undated).

Microdrop Instruction Manual, Microdrop Gesellschaft für Mikrodosiersysteme mbH, MD–K–130SP/140H/135/150 and Drive electronics MD–E–204, May 1994.

Microdrop Instruction Manual, Microdrop Gesellschaft für Mikrodosiersysteme mbH, AD–E–130, Sep. 1995.

Microdrop Literature, "Flussigkeiten mikrofein dosieren" Gesellschaft for Mikrodosiersysteme mbH, 1994 (in the German language).

Microdrop literature, "Microdosing in the picoliter range with piezo technology" sales brochure from Microdrop Gesellschaft für Mickrodosiersysteme mbH, Oct. 1995.

Pimbley "Satellite Droplet Formation in a Liquid Jet" pp. 21–30, Satellite Formation, IBM J. Res. Develop. (Undated).

Plunkett, Matthew J. et al., "Combinatorial Chemistry and New Drugs," Scientific American, Apr. 1997, p. 69–73.

Schober, A., et al., "Accurate High–Speed Liquid Handling of Very Small Biological Samples," BioTechniques, vol. 15, No. 2 (1993), p, 324–329.

Twardeck "Effect of Parameter Variations on Drop Placement in an Electrostaic Ink Jet Printer" pp. 31–36, IBM J. Res. Develop. (Undated).

Zengerle et al., "Carbon Dioxide Priming of Micro Liquid Systems," *IEEE* (1995), pp. 340–343.

* cited by examiner

DISPENSING LIQUID DROPS ONTO POROUS BRITTLE SUBSTRATES

RELATED APPLICATIONS

This application is a continuation-in-part of U.S. application Ser. No. 09/056,233, filed Apr. 7, 1998, U.S. Pat. No. 6,203,759, which is a conventional application of provisional U.S. Application No. 60/041,861, filed Apr. 8, 1997, and provisional U.S. Application No. 60/067,665, filed Dec. 5, 1997, which is a continuation-in-part of U.S. application Ser. No. 08/656,455, filed May 31, 1996, abandoned.

BACKGROUND OF THE INVENTION

This invention relates to aspirating and dispensing small volumes of liquids. In particular, it relates to automatic aspirating and dispensing of small volumes of liquids onto porous brittle substrates.

The advances in biochemical technology have led to development of miniature reaction sites generally located on brittle, thin wafers, having hundreds of such reaction sites, each capable of holding small chemical and/or biological samples. The wafers are porous, with narrow pores extending into the wafer and generally normal to the plane of the surface. In order to deposit the sample onto a selected reaction site, the tip of the dispenser must be brought in close proximity with the wafer. Placing the tip of the dispenser close to the surface of the wafer introduces the risk of the tip touching the surface of the reaction medium. Since the reaction media are generally brittle, any contact could break the wafer and render useless all samples deposited on that wafer. If the contact does not break the wafer, the tip of the dispenser can abrade a coating on the vessel or destroy its confirmation. Contact with the wafer can also cause the liquid to spread on the surface. Therefore, there is a need for a system and method for dispensing small quantities of liquids containing biological and/or chemical substances in a precise location on brittle wafers without having to bring the dispenser tip into close proximity with the reaction site.

Another disadvantage of conventional methods for dispensing liquids onto wafers is that the drop at the end of the dispenser tip is placed in contact with the surface of the wafer. In order to deposit the sample in a precise location on the wafer, a drop of liquid is formed at the tip of the dispenser over the surface of the reaction site. The contact between the drop and the reaction site causes the drop to separate from the dispensing tip. The transfer of a drop of sample liquid in this manner is difficult to control because surface tension effects at the dispenser tip and the wafer surface affect the amount of liquid dispensed. As a result, there is a need for a method and system of precisely depositing small amounts of liquid at specific locations of a reaction medium. It is also necessary to have a means of dispensing liquids where the size of the drop is accurately controlled and not a function of the properties of the liquid and substrate.

One object of the present invention is to provide a system and method for accurately aspirating and dispensing submicroliter volumes of liquid onto a reaction site of a wafer without bringing the drop in contact with the surface of the wafer. Another object of the present invention is to provide a system and method for accurately verifying the volume of liquid dispensed onto the substrate.

Still another object of the present invention is to provide a system and method for dispensing subnanoliter droplets of liquid by ejecting them onto reaction sites with pore sizes 10 to 10,000 times smaller than the diameter of the drop.

Yet another object of the present invention is to provide a system and method for accurately depositing micron size droplets of liquid onto a porous substrate having submicron size pores.

Still another object of the present invention is to provide a system and method for ejecting droplets of liquid with diameters of less than 100 microns onto porous substrates with pore sizes 10 to 10,000 times smaller than the diameter of the drops. The size of the spot created by the drop on the substrate is only slightly larger than the diameter of the drop.

A further object of the present invention is to provide a system and method for aspirating and dispensing microvolumes of liquid onto porous reaction sites and accurately measuring the amount of liquid dispensed, regardless of the properties (e.g., viscosity or hydrophilicity) of the transfer liquid.

Another object of the present invention is to provide a system for aspirating and ejecting microvolumes of liquid containing chemically or biologically active s substances onto a porous reaction site of a wafer.

A still further object of the present invention is to provide for a real time monitoring of the dispensing of single 100 micron or smaller drops of liquid onto porous reaction sites of wafers.

Still another object of the present invention is to eject a plurality of drops of liquid onto a porous reaction site of a thin wafer.

Yet another object of the present invention is to eject onto a porous reaction site at least one small drop of liquid and measure, in real time, the volume of the dispensed liquid.

Other objects and advantages of the present invention will be apparent to those skilled in the art upon studying this application.

SUMMARY OF THE INVENTION

In accordance with one aspect of the present invention, 1 to 100 micron range drops of liquid are accurately deposited onto a porous reaction site having pores about 10 to about 10,000 times smaller than the size of the drop. The drops are dispensed by ejection from a tube using a piezoelectric element where the distance of the tip of the tube to the surface of the wafer is greater than the diameter of the drops. Accordingly, the drops do not touch the surface of the wafer prior to being ejected. Therefore, the properties of the liquid and the surface of the wafer do not affect the size of the drop that is ejected. The ejected drop forms a spot which is nearly the same diameter as that of the ejected droplet because it penetrates the narrow pores of the wafer.

In one aspect of the invention, a system and method for aspirating and ejecting subnanoliter drops of liquid onto a porous reaction site and detecting a pressure change resulting from the droplet ejection is presented. A known volume of a compressible fluid, e.g., a gas such as air, facilitates measuring small changes in system pressure which correlate to the volume of the transfer liquid which has been dispensed.

In accordance with another aspect of the present invention, a system and method for aspirating and ejecting subnanoliter drops of liquid onto a porous reaction site, detecting a pressure change resulting from ejection of a drop of a transfer liquid, and generating an electrical signal which indicates that single drops of liquid are dispensed at millisecond intervals is presented. By eliminating all compressible fluids (gases) from the liquid in the system, the ejection of picoliter size drops can be detected by the present invention. The dispensed drops are generally in the range of from about 5 to about 500 picoliters, often about 100 to about 500 picoliters. The pores of the wafer are in the submicron range.

In accordance with yet another aspect of the present invention, subnanoliter droplets of liquid are ejected onto porous sites of a thin wafer and the volume of the drops is measured in real time. Electrical signals indicating transient pressure changes in the transfer liquid upon dispensing liquid drops (in the range of from about 5 to about 500 picoliters, preferably about 100 to about 500 picoliters) can be detected when the liquid in the enclosed volume of the dispenser is connected to a liquid reservoir. As long as substantially all compressible fluids (gases) are kept out of the dispensing conduit (which communicates through a restricted passage to the liquid reservoir), the pressure sensor of the system of the present invention can detect dispensing a single drop of liquid in the range of from about 5 to about 500 picoliters, preferably about 100 to about 500 picoliters. The pressure change resulting from ejection of such a drop occurs in a time period long enough for the pressure change to be detectable, but short enough to complete the cycle before the next drop is ejected.

Other aspects of the present invention will become apparent to those skilled in the art upon studying this disclosure.

DESCRIPTION OF ILLUSTRATIVE EMBODIMENTS

Figure 1:
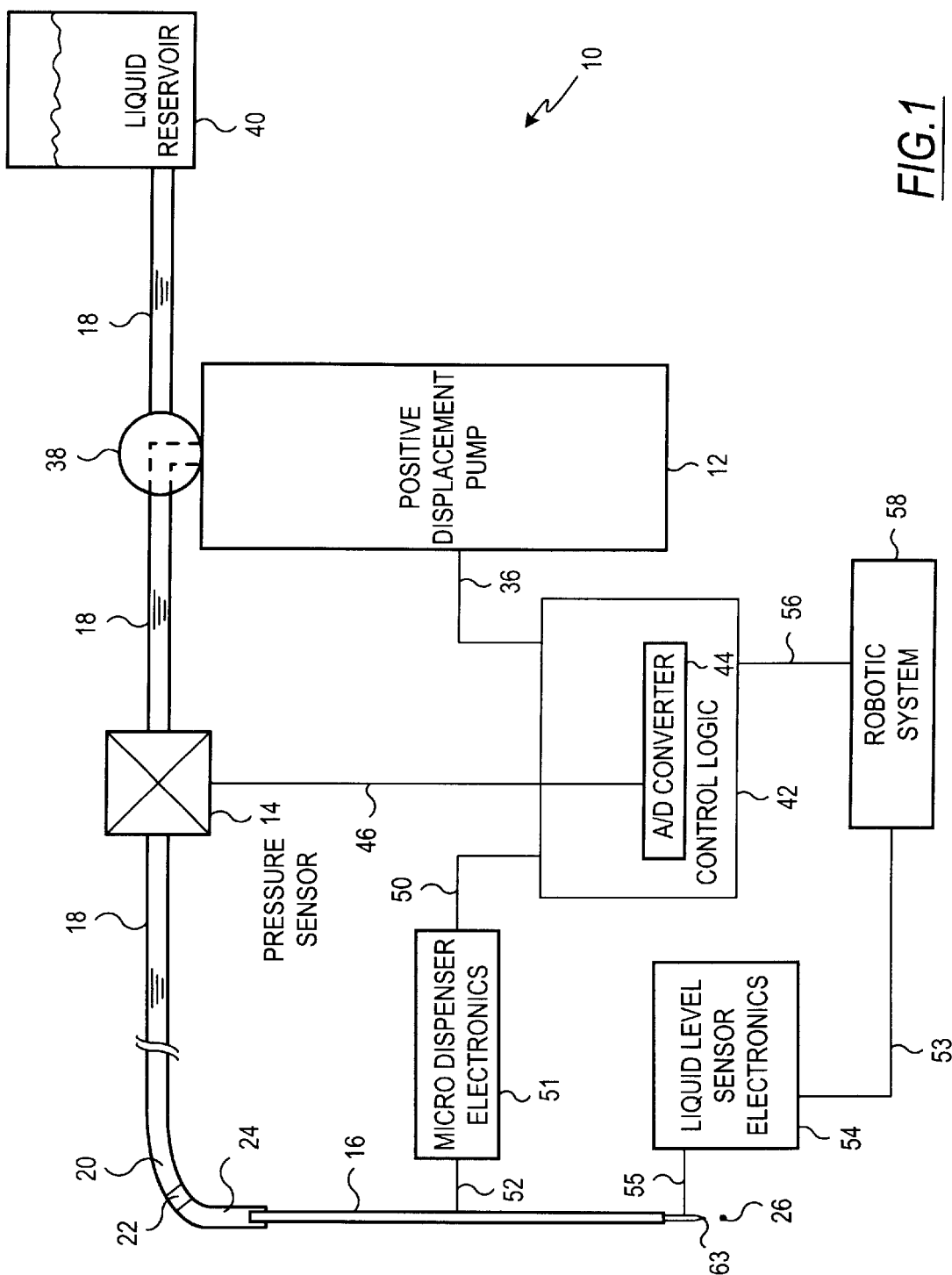
FIG. 1 is a block diagram of a system for aspirating and dispensing microvolumes of liquid onto a reaction site of a thin plate, illustrating the first embodiment of the present invention.

The present invention relates to an application for the aspirating and dispensing apparatus described in parent application Ser. No. 09/056,233, U.S. Pat. No. 6,203,759.
Description of Wafers for Use in Present Invention As used herein, the term "wafer" includes any object which has a porous site on at least one of its surfaces. The wafers suitable for use in connection with the present invention have sites with pore size significantly smaller than the size of the drops of liquid deposited onto the wafers. Generally, the pore size of the sites are from about 10 to about 10,000 times smaller than the diameter of the drops which are deposited thereon. If the drops of liquid are in the 10 to 100 micron range, the pore size should be in the micron or the submicron range. Wafers suitable for use in the present invention include those that have specific, defined reaction sites and whose surface is partially or wholly porous. Such wafers include membranes, slides, micromachined silicon, porous gels, and polymers. Generally, the pore size of the reaction sites are in the range of from about 0.1 to about 10 microns, preferably from about 0.25 to about 1 micron. One example of a wafer which is suitable for use in the present invention is the Anapore membrane, marketed by The Whatman Companies. Other wafers suitable for use in the present invention include the Hydrogel chip, manufactured by Packard Instrument Company, Downers Grove, Ill.

One example of such porous wafers is found in U.S. Pat. No. 5,843,767. While Example 5 of the '767 patent describes a system for depositing droplets on is porous wafers, there is no recognition of the problem discussed above by the present inventors and method disclosed herein to solve that problem.
Description of a First Aspirating and Dispensing Apparatus The system constructed in accordance with the first aspirating and dispensing apparatus of the present invention includes a system liquid and a transfer liquid separated by a known volume of compressible fluid, e.g., a gas such as air ("air gap"). The air gap facilitates measuring small changes in pressure in the system liquid. The change in pressure is proportional to the volume of transfer liquid dispensed. One preferred system liquid is deionized water. As a result of capillary forces, each time a droplet in the microvolume dispensing range is dispensed, the transfer liquid will return to its prior position inside the microdispenser. The specific volume of the air gap will be increased proportionally to the amount of transfer liquid dispensed. The result is a decrease in pressure in the system liquid line which is measured with a highly sensitive piezoresistive pressure sensor. The pressure sensor transmits an electric signal which controls circuitry. The electric signal is converted into a digital form which is indicative of the volume of transfer liquid dispensed. An advantage of the present invention is its insensitivity to the viscosity of the transfer liquid. The pressure change in the system liquid corresponds to the microvolume dispensed, without being dependent on the viscosity of the dispensed liquid.

The first aspirating and dispensing apparatus of the present invention provides a microvolume liquid handling system which includes a positive displacement pump operated by a stepper motor, a piezoresistive pressure sensor, and an electrically controlled microdispenser that utilizes a piezoelectric transducer bonded to a glass capillary. The microdispenser is capable of rapidly and accurately dispensing sub-nanoliter ("nl") sized droplets by forcibly ejecting the droplets from a small nozzle, this process is known as "drop-on-demand." Specifically, the dispenser of the present invention dispenses drops in the range of from about 5 to about 500 picoliters, preferably from about 100 to about 500 picoliters.

To provide the functionality of an automated liquid handling system, the microdispensers in all preferred embodiments are mounted onto a 3-axis robotic system that is used to position the microdispensers at specific locations required to execute the desired liquid transfer protocol.

Referring first to FIG. 1, a first microvolume liquid handling system 10 is illustrated, and includes a positive displacement pump 12, a pressure sensor 14, and a microdispenser 16. Tubing 18 connects the positive displacement pump 12 to the pressure sensor 14 and the pressure sensor 14 to the microdispenser 16. The positive displacement pump 12 moves a system liquid 20 through the pressure sensor 14 and the microdispenser 16. After the system 10 is loaded with system liquid 20, an air gap 22 of known volume is provided. An amount of transfer liquid 24 is drawn into the microdispenser 16 in a manner described below. The transfer liquid 24 can contain one or more biologically or chemically active substances of interest. Preferably, the microdispenser 16 expels (or, synonymously, "shoots") sub-nanoliter size individual droplets 26 which are very reproducible. The expelled droplets 26 of transfer liquid 24 are generally in the range of about 5 to about 500 picoliters, preferably about 100 to about 500 picoliters per droplet 26. For example, if one desires to expel a total of 9 nanoliters of transfer liquid 24, the microdispenser 16 will be directed to expel 20 droplets 26, each having a volume of 0.45 nanoliters. Droplet 26 size can be altered by varying the magnitude and duration of the electrical signal applied to the microdispenser 16. Other factors affecting droplet size include: size of the nozzle opening at the bottom of the microdispenser, pressure at the microdispenser inlet, and certain properties of the transfer liquid.

Figure 2:
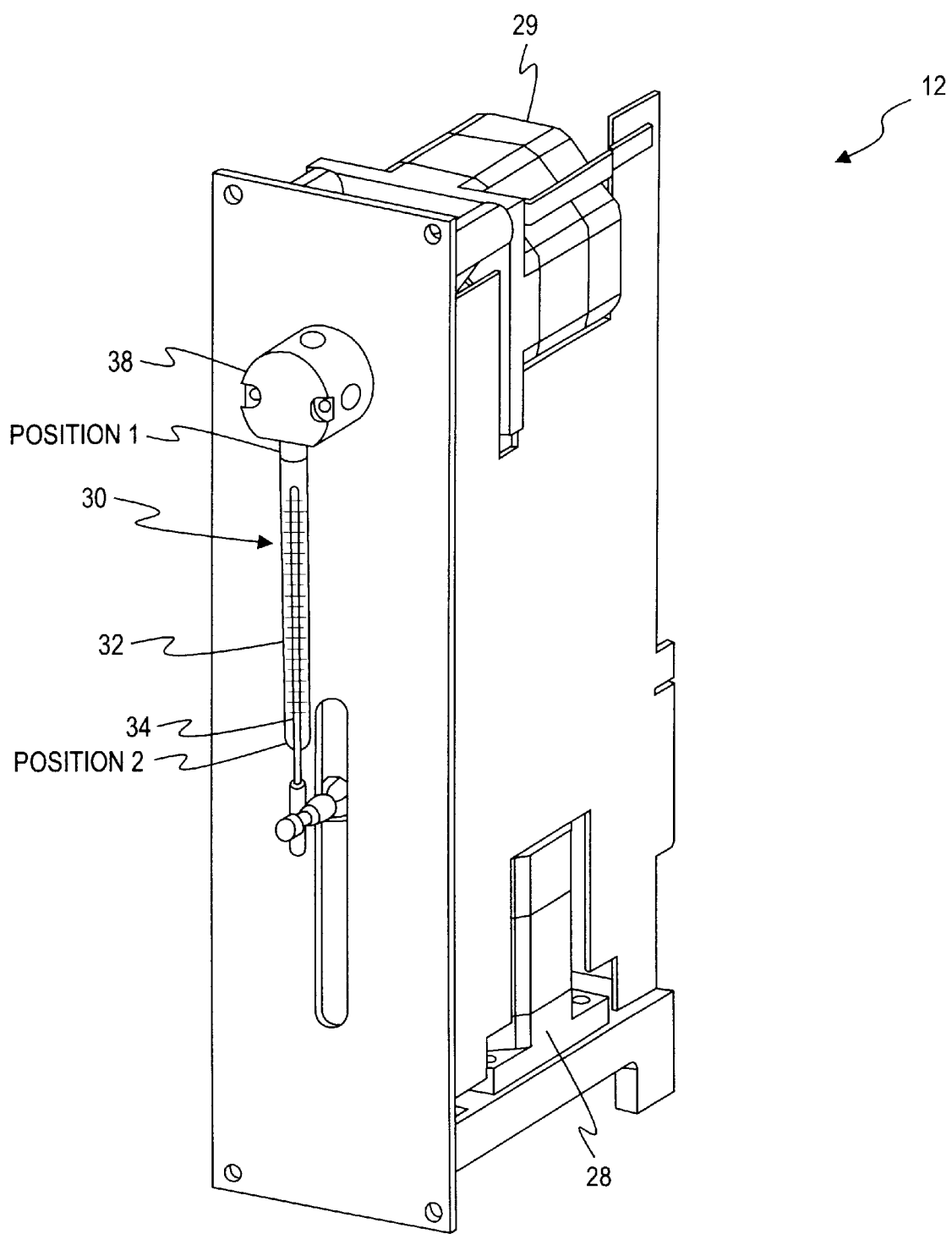
FIG. 2 is a schematic of a positive displacement pump illustrating an aspect of the first embodiment of the present invention.

Referring now to FIGS. 1 and 2, in one preferred embodiment, the positive displacement pump 12 is an XL 3000 Modular Digital Pump, manufactured by Cavro Scientific Instruments, Inc., Sunnyvale, Calif. The positive displacement pump 12 includes stepper motor 28, stepper motor 29, and a syringe 30. The syringe 30 includes a borosilicate glass tube 32 and a plunger 34 which is mechanically coupled through a series of gears and a belt (not shown) to the stepper motor 28. Stepper motor 28 motion causes the plunger 34 to move up or down by a specified number of discrete steps inside the glass tube 32. The plunger 34 forms a liquid-tight seal with the glass tube 32. In one preferred embodiment, syringe 30 has a usable capacity of 250 microliters, which is the amount of system liquid 20 the plunger 34 can displace in one full stroke. Depending on the selected mode of operation, the stepper motor 28 is capable of making 3,000 or 12,000 discrete steps per plunger full 34 stroke. In one preferred embodiment, the stepper motor 28 is directed to make 12,000 steps per plunger 34 full stroke, with each step displacing approximately 20.83 nanoliters of system liquid 20. In one preferred embodiment, the system liquid 20 utilized is deionized water.

Digitally encoded commands cause the stepper motor 28 within the positive displacement pump 12 to aspirate discrete volumes of liquid into the microdispenser 16, wash the microdispenser 16 between liquid transfers, and control the pressure in the system liquid 20 line for microvolume liquid handling system 10 operation. The positive displacement pump 12 is also used to prime the system 10 with system liquid 20 and to dispense higher volumes of liquid through the microdispenser 16, allowing the dilution of certain system liquids. The positive displacement pump 12 can also work directly with transfer liquid 24. Thus, if desired, transfer liquid 24 can be used as system liquid 20 throughout the microvolume liquid handling system 10.

To prime the microvolume liquid handling system 10, the control logic 42 first directs a 3-axis robotic system 58 through electrical wire 56 to position the microdispenser 16 over a wash station contained on the robotic system 58. In one preferred embodiment, the microvolume liquid handling system 10 includes, and is mounted on, a 3-axis robotic system, the MultiPROBE CR10100, manufactured by Packard Instrument Company. The positive displacement pump 12 includes a valve 38 for connecting a system liquid reservoir 40 to the syringe 30. An initialization control signal is transmitted through the electrical cable 36 to the pump 12 by control logic 42. This causes the valve 38 to rotate (by means of stepper motor 29), connecting the syringe 30 with the system liquid reservoir 40. The control signal also causes the stepper motor 28 to move the plunger 34 to its uppermost position (Position 1 in FIG. 2) in the borosilicate glass tube 32. The next command from the control logic 42 causes the stepper motor 28 to move the plunger 34 to its lowermost position (Position 2 in FIG. 2) in the tube 32 and to extract system liquid 20 from the is system reservoir 40. Another command from the control logic 42 directs the valve 38 to rotate again, causing the syringe 30 to be connected with the tubing 18 that is, in turn, connected to the pressure sensor 14. In one preferred embodiment, the tubing 18 employed in the microvolume liquid handling system 10 is Natural Color Teflon Tubing, manufactured by Zeus Industrial Products, Inc., Raritan, N.J., with an inner diameter of 0.059 inches and an outer diameter of 0.098 inches. The next command from the control logic 42 to the positive displacement pump 12 causes the system liquid 20 inside the syringe 30 to be pushed into the microvolume liquid handling system 10 towards the pressure sensor 14. Because the microvolume liquid handling system 10 typically requires about 4 milliliters of system liquid to be primed, the sequence of steps described above must be repeated about 16 times in order to completely prime the microvolume liquid handling system 10.

The control logic 42 receives signals from the pressure sensor 14 through an electrical line 46. The signals are converted from an analog form into a digital form by an A/D (analog to digital) converter 44 and used by the control logic 42 for processing and analysis. In one preferred embodiment, the A/D converter is a PC-LPM-16 Multifunction I/O Board, manufactured by National Instruments Corporation, Austin, Texas. At various points in the liquid transfer process described herein, the control logic 42 receives signals from the pressure transducer 14, and sends command signals to the pump 12, microdispenser electronics 51, and the 3-axis robotic system 58. Within the control logic 42 exist the encoded algorithms that sequence the hardware (robotic system 58, pump 12, and microdispenser electronics 51) for specified liquid transfer protocols, as described herein. Also within the control logic 42 are the encoded algorithms that process the measured pressure signals to verify and quantify microdispenser, perform diagnostics on the state of the microvolume liquid handling system, and automatically perform a calibration of the microdispenser for any selected transfer liquid 24.

The pressure sensor 14 detects fluctuations in pressure that occur with priming the microvolume liquid handling system 10, aspirating transfer liquid 24 with a pump 12, dispensing droplets 26 with the microdispenser 16, and washing of the microdispenser 16 with a pump 12. In one preferred embodiment, the pressure sensor 14 is a piezoresistive pressure sensor, part number 26PCDFG6G, manufactured by Microswitch, Inc., a division of Honeywell, Inc., Freeport, Ill. Also included with the pressure sensor 14 in the block diagram in FIG. 1 is electrical circuitry which amplifies the analog pressure signal from the pressure sensor. The pressure sensor 14 converts pressure into electrical signals which are driven to the A/D converter 44 and used by the control logic 42. For example, when the microvolume liquid handling system 10 is being primed, the pressure sensor 14 sends electrical signals which are analyzed by the control logic 42 to determine whether they indicate partial or complete blockage in the microdispenser 16.

Once the microvolume liquid handling system 10 is primed, the control logic 42 sends a signal through electrical wire 56 which instructs the robotic system 58 to position the microdispenser 16 in air over the transfer liquid 24. The control logic 42 instructs the stepper motor 28 to move the plunger 34 down, aspirating a discrete quantity of air (air gap), e.g., 50 microliters in volume, into the microdispenser 16. The control logic 42 then instructs the robotic system 58 to move the microdispenser 16 down until it makes contact with the surface of the transfer liquid 24 (not shown). Contact of the microdispenser 16 with the surface of the transfer liquid 24 is determined by a capacitive liquid level sensing system (U.S. Pat. No. 5,365,783). The microdispenser is connected by electrical wire 55 to the liquid level sense electronics 54. When the liquid level sense electronics 54 detects microdispenser 16 contact with the transfer liquid 24 surface, a signal is sent to the robotic system 58 through electrical wire 53 to stop the downward motion.

The control logic 42 instructs the pump 12 to move the plunger 34 down to aspirate the transfer liquid 24 into the microdispenser 16. To ensure that the transfer liquid is successfully drawn into the microdispenser, the pressure signal is monitored by control logic. If a problem, such as an abnormal drop in pressure due to partial or total blockage of the microdispenser is detected, the control logic 42 will send a stop movement command to the pump 12. The control logic 42 will then proceed with an encoded recovery algorithm. Note that the transfer liquid 24 can be drawn into the microvolume liquid handling system 10 up to the pressure sensor 14 without the threat of contaminating the pressure sensor 14. Additional tubing can be added to increase transfer liquid 24 capacity. Once the transfer liquid 24 has been aspirated into the microdispenser 16, the control logic 42 instructs the robotic system 58 to reposition the microdispenser 16 above the chosen target, e.g., a microtiter plate or a wafer.

In one preferred embodiment, the microdispenser 16 is the MD-K-130 Microdispenser Head, manufactured by Microdrop, GmbH, Norderstedt, Germany.

Figure 3:
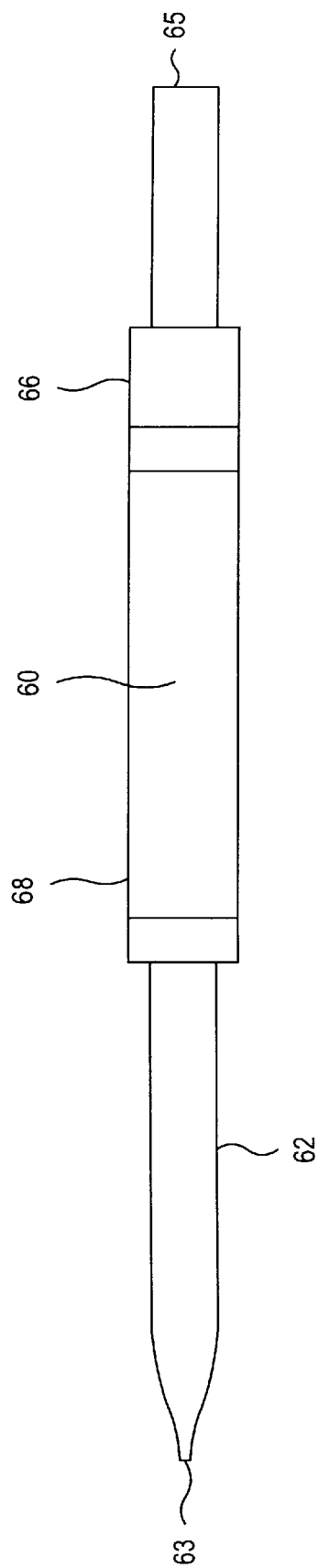
FIG. 3 is side plan view of a microdispenser including a piezoelectric transducer.

As illustrated in FIG. 3, the microdispenser 16 consists of a piezoceramic tube 60 bonded to a glass capillary 62. The piezoceramic tube has an inner electrode 66 and an outer electrode 68 for receiving analog voltage pulses which cause the piezoceramic tube to constrict. Once the glass capillary 62 has been filled with transfer liquid 24, the control logic 42 directs the microdispenser electronics 51 to send analog voltage pulses to the piezoelectric transducer 60 by electrical wire 52. In one preferred embodiment, the microdispenser electronics 51 is the MD-E-201 Drive Electronics, manufactured by Microdrop, GmbH. The microdispenser electronics 51 control the magnitude and duration of the analog voltage pulses, as well as the frequency at which the pulses are sent to the microdispenser 16. Each voltage pulse causes a constriction of the piezoelectric transducer 60 which, in turn, deforms the glass capillary 62. The deformation of the glass capillary 62 produces a pressure wave that propagates through the transfer liquid 24 to the microdispenser nozzle 63, where one highly accelerated droplet 26 of transfer liquid 24 is emitted. The size of these droplets 26 has been shown to be very reproducible. The high acceleration of the transfer liquid 24 minimizes or eliminates problems caused by transfer liquid 24 surface tension and viscosity, thus allowing extremely small (e.g., 5 picoliter) droplets 26 to be expelled from the nozzle. Use of the microdispenser 16 to propel droplets 26 out of the nozzle circumvents problems encountered in the liquid transfer technique referred to "touchoff." In the touchoff technique, a droplet 26 is held at the end of a nozzle and is deposited onto a target surface by bringing that droplet 26 into contact with the target surface while it is still suspended from the microdispenser 16. Such a contact process is susceptible to unacceptable volume deviations as a result of surface tension, viscosity and wetting properties of the microdispenser 16 and the target surface. The present invention avoids the problems of the contact process because the droplets 26 are expelled out of the microdispenser 16 at a velocity of several meters per second. The total desired volume is dispensed by the present invention by specifying the number of droplets 26 to be expelled. Because thousands of droplets 26 can be emitted per second from the microdispenser 16, the desired microvolume of transfer liquid 24 can rapidly be dispensed.

In one preferred embodiment, the lower section of the glass capillary 62, located between the piezoelectric transducer 60 and the nozzle 63, is plated with a conductive material, typically platinum or gold. The use of this material provides an electrically conductive path between the microdispenser 16 and the liquid level sense electronics 54. In one preferred embodiment, the glass capillary 62 has an overall length of 73 millimeters and the nozzle 63 has an internal diameter of 75 micrometers.

To dispense microvolume quantities of transfer liquid 24, analog voltage pulses are sent to the microdispenser 16, thus emitting droplets 26 of liquid. Capillary forces acting on the transfer liquid 24 replace the volume of transfer liquid 24 emitted from the microdispenser 16 with liquid from the tubing 18. Since the transfer liquid-air gap system liquid column terminates at a closed end in the positive displacement pump 12, however, there is a corresponding drop in the system liquid 20 line pressure as the air gap 22 is expanded. This may be seen in FIG. 4 of parent application Ser. No. 09/056,233 U.S. Pat. No. 6,203,759. The magnitude of the pressure drop is a function of the size of the air gap 22 and the volume of the liquid dispensed.

With an air gap 22 of known volume, the pressure change as detected by the pressure sensor 14 is proportional to the volume dispensed. Thus, from the pressure change measured by the pressure sensor 14, the control logic determines the volume of transfer liquid 24 that was dispensed. In one preferred embodiment of the present invention, depending on the properties of the transfer liquid, it is preferable that the drop in pressure not exceed approximately 30 to 40 millibars below ambient pressure. If the amount of transfer liquid 24 dispensed is sufficient to drop the pressure more than 30 to 40 millibars, the pressure difference across the microdispenser 16 (i.e., the is difference between the ambient pressure acting on the nozzle 63 and the pressure at the capillary inlet 65) will be sufficient to force the transfer liquid 24 up into the tubing 18. This will preclude further dispensing. There is a maximum amount of transfer liquid 24 that can be dispensed before the control logic 42 is required to command the pump 12 to advance the plunger 34 to compensate for the pressure drop. This maximum volume is determined by the desired dispense volume and the size of the air gap 22. Conversely, the size of the air gap 22 can be selected based on the desired dispense volume so as not to produce a pressure drop exceeding 30 to 40 millibars below ambient pressure. It is also within the scope of the present invention to advance the plunger 34 while the microdispenser 16 is dispensing, thereby rebuilding system liquid 20 line pressure so that the microdispenser 16 can operate continuously.

The change in system liquid 20 pressure is used to verify that the desired amount of transfer liquid 24 was dispensed. A second verification of the amount of transfer liquid 24 that was dispensed is made by the control logic 42 that monitors the system liquid 20 line pressure while directing the pump 12 to advance the syringe plunger 34 upwards towards Position 1. The syringe plunger 34 is advanced until the system liquid 20 line pressure returns to the initial (pre-dispense) value. Because the control logic 42 tracks the displaced volume, the plunger 34 moves (20.83 nanoliters per stepper motor 28 step) and a second confirmation of the volume dispensed is made, thus adding robustness to the system. After a second dispensing verification, the system liquid 20 line pressure is now at the correct value for the next dispensing action if a multidispense sequence has been specified.

Once the transfer liquid 24 dispensing has been completed, the control logic 42 causes the robotic system 58 to position the microdispenser 16 over the wash station. The control logic 42 then directs pump 12 and robotic system 58 in a wash protocol that disposes of any transfer liquid 24 left in the microdispenser 16. This protocol also results in washes to the internal surface of the glass capillary 62 and the external surface in the nozzle 63 area that was exposed to transfer liquid 24. The wash liquid can either be system liquid 20 or any other liquid placed onto the deck of the robotic system 58. The wash protocol is designed to minimize cross-contamination of different transfer liquids 24 used during different dispensing sessions. Towards this end, it is also possible to use a high frequency pulsing of the transducer 60 to facilitate washing of the microdispenser 16. This is accomplished using the control logic 42 to direct the microdispenser electronics 51 to send electrical pulses to the microdispenser at a frequency in the range of from about 1 to about 20 Khz (the preferred resonant frequency of the microdispenser 16 is believed to be approximately 12 kilohertz). The resonant frequency of the microdispenser coincides with the resonant frequency of the microdispenser 16—transfer liquid 24 system. Pulsing the piezoelectric transducer 60 at the above frequencies causes the interior surfaces of the glass capillary 62 to vibrate vigorously. System liquid 20, or a special cleaning and/or neutralizing liquid, is used to flush out the microdispenser 16 while the piezoelectric transducer 60 is activated at the above-described frequencies. Cleaning with high frequency pulsing is more efficient at dislodging and eliminating matter adhering to the microdispenser 16. For example, it has been shown in a number of test cases that such cleaning caused a 200 to 500% improvement (depending on the contaminant) in the reduction of residual matter in the microdispenser 16 compared to cleaning without such pulsing.

Pulsing of the microdispenser 16 is also used to prevent, minimize or alleviate clogging of the nozzle of the microdispenser. For example, when transfer liquid is being aspirated into the microdispenser 16, it must pass through the relatively narrow nozzle 63 in the glass capillary 62. Matter in the transfer liquid 24 often comes into contact with the nozzle's 63 surfaces, permitting the matter to adhere to the nozzle 63. In biochemical applications, one widely used matter added to the transfer liquid 24 is polystyrene spheres. These spheres typically range from 1 micron to over 30 microns, and may be uncoated or coated with magnetic ferrites, antigens or other materials. The relatively large size of the polystyrene spheres with regard to nozzle 63 diameter, in combination with their sometimes glutinous coatings, can cause the spheres to adhere to the nozzle 63. It has been discovered that if the piezoelectric transducer 60 is excited at high frequency while the microdispenser 16 is being loaded (i.e., transfer liquid 24 is being aspirated into the microdispenser 16), clogging is prevented or minimized. Thus, high frequency pulsing of the microdispenser 16 prevents or diminishes clogging of the nozzle 63 by materials in the transfer liquid 24.

Anytime a transfer liquid 24 containing dissolved or suspended materials passes through the nozzle 63, the possibility of clogging occurs. Not only is clogging a problem during aspiration of transfer liquid 24 into the microdispenser 16 as described above, but it is also a problem when transfer liquid is dispensed from the high frequency pulsing of the microdispenser 16. Droplet dispensing by the piezoelectric transducer can reduce buildup of materials adhering to the nozzle 63 and, thus, prevent clogging in some instances. Even if substantial clogging does occur, high frequency pulsing of the microdispenser 16 by the piezoelectric transducer 60 will substantially clear the clogging materials from the nozzle 63. The key advantage to this cleaning strategy is continuous instrument operation without the delays associated with alternate cleaning procedures. In short, system downtime is reduced, making the microvolume liquid handling system 10 more efficient.

In the above description of the invention, the control of the microdispenser 16 occurs via electrical pulses from the microdispenser electronics 51, with each pulse resulting in an emitted droplet 26 of transfer liquid 24. It is also within the scope of the invention to control the microdispenser 16 by monitoring the pressure sensor 14 signal in real time, and continuing to send electrical pulses to the microdispenser 16 until a desired change in pressure is reached. In this mode of operation, the PC-LPM-16 Multifunction I/O Board that contains the A/D converter 44 is instructed by control logic 42 to send electrical pulses to the microdispenser electronics 51. Each pulse sent by the Multifunction I/O Board results in one electrical pulse sent by the microdispenser electronics 51 to the microdispenser 16, emitting one droplet 26 of transfer liquid 24. The control logic 42 monitors the pressure sensor 14 signal as dispensing is in progress. Once the desired change in pressure has been attained, the control logic 42 directs the Multifunction I/O Board to discontinue sending electrical pulses.

This mode of operation is employed if a "misfiring" of microdispenser 16 has been detected by control logic 42.

It is also within the scope of the invention for the microvolume liquid handling system 10 to automatically determine the size of the emitted droplets 26 for transfer liquids 24 of varying properties. As heretofore mentioned, emitted droplet 26 size is affected by the properties of the transfer liquid 24. Therefore, it is desirable to be able to automatically determine emitted droplet 26 size so that the user need only specify the total transfer volume to satisfy the user requirements. In the encoded autocalibration algorithm, once the system 10 is primed, an air gap 22 and transfer liquid 24 are aspirated, and the control logic 42 instructs the microdispenser electronics 51 to send a specific number of electrical pulses, e.g., 1000, to the microdispenser 16. The resulting drop in pressure sensor 14 signal is used by the control logic 42 to determine the volume of transfer liquid 24 that was dispensed. The control logic verifies the volume of liquid dispersed by tracking the volume displaced by the movement of the plunger 34. The system subsequently restores the liquid line pressure to the pre-dispense value.

The microvolume liquid handling system 10 illustrated in FIG. 1 depicts a single microdispenser 16, pressure sensor 14, and pump 12. It is within the spirit and scope of this invention to include embodiments of microvolume liquid handling systems that have a multiplicity (e.g., 4, 8, 96) of microdispensers 16, pressure sensors 14, and pumps 12. It is also within the spirit and scope of this invention to include embodiments of microvolume liquid handling systems that have a multiplicity of microdispensers 16, pressure sensors 14, valves 38, and one or more pumps 12.

Description of a Second Aspirating and Dispensing Apparatus

Figure 7:
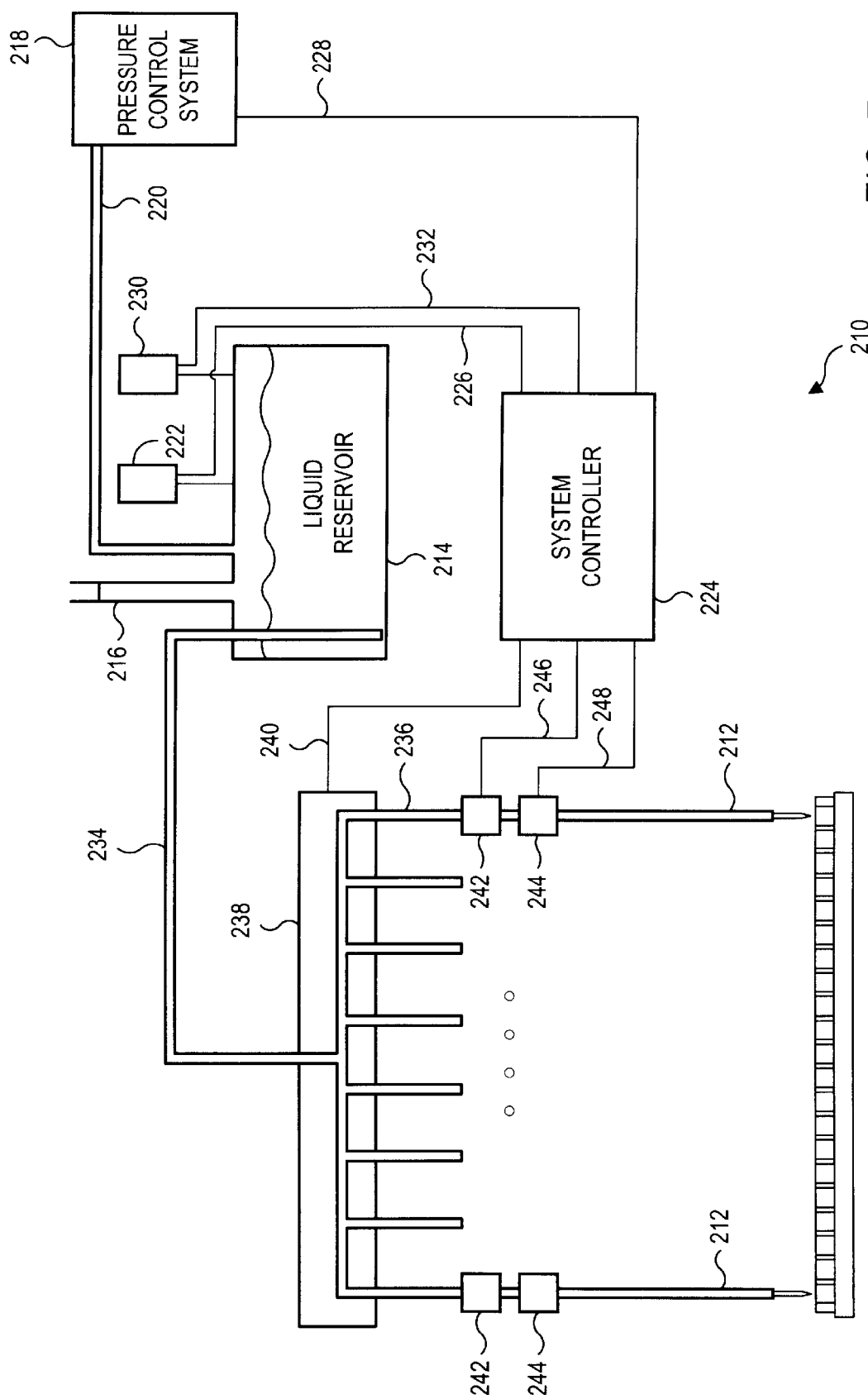
FIG. 7 is a block diagram of the system for aspirating and dispensing microvolumes of liquid illustrating the second embodiment of the present invention.

In FIG. 7, another aspirating and dispensing apparatus 210 is shown. This embodiment, which is preferred when the number of microdispensers employed is equal to or greater than eight, also realizes the aforementioned objectives. The second apparatus is similar to the first shown in FIG. 1, except that the positive displacement pump (which includes a valve as described below), the stepper motor, and the piezoresistive pressure sensor are replaced with a pressure control system for supplying and controlling system liquid pressure. This embodiment also employs a plurality of flow sensors for detecting liquid flow, as well as pressure in the system liquid which is present in the connecting tubing that is coupled to each microdispenser. It also employs a plurality of valves (such as solenoid or microfabricated valves), each valve coupling each microdispenser to a system reservoir in the pressure control system. In this apparatus, a system liquid reservoir 214 is used to supply system liquid 20 to all the microdispensers 212, thus eliminating the separate pump and pressure sensor for each microdispenser 212 utilized in the first apparatus. Note that first and second embodiments are otherwise identical in structure and operation except as described herein. The precise number of microdispensers employed is a function of the user's dispensing requirements.

With regard to the second embodiment, the system liquid reservoir 214 receives system liquid 20, typically deionized water or dimethyl sulfoxide (DMSO), through an intake tube 216 which contains a cap (not separately shown). The cap on the intake tube 216 is removed to enable the sealed system liquid reservoir 214 to receive system liquid 20 when the cap is off, and seals the system liquid reservoir 214 shut when the cap is on so that the system liquid reservoir 214 can be maintained at a desired pressure. Pressure in the system liquid reservoir 214 is maintained by a pressure control system 218 through the use of pressure control tubing 220. The pressure control system 218 includes an electrically controlled pump capable of accurately increasing or decreasing pressure in the system liquid reservoir 214. A pressure sensor 222 mounted on the system liquid reservoir 214 senses pressure in the system liquid reservoir 214 and transmits an electrical signal indicative of that pressure to a system controller 224 through an electrical conductor 226. The system controller 224 contains a digital signal processor board and other electronics (not shown) which enable monitoring of various electrical signals, execution of control software code, and control of the microvolume liquid handling system 210. The system adjusts the pressure of the system liquid 20 and, correspondingly, the pressure of the transfer liquid 24 via an electrical conductor. A pressure relief valve 230 is mounted on the system liquid reservoir 214. The pressure relief valve 230 releases pressure from the system liquid reservoir 214 when the pressure exceeds a predetermined safety threshold. In one embodiment, the pressure relief valve 230 can also be opened by the system controller 224 which is connected to the pressure relief valve 230 by a wire 232.

During operations, the system controller 224 directs the pressure control system 218 to maintain one of three different pressure levels in the system reservoir 214 with regard to ambient atmospheric pressure. Each of the three pressure levels corresponds to a different phase of operation of the microvolume liquid handling system 210. The three different pressure levels include a positive pressure, a high negative pressure, and a low negative pressure. Prior to dispensing, positive pressure is used to clean the microdispenser. High frequency pulsing of the microdispensers 212 is also employed in the manner described above. After the microdispensers 212 are relatively clean, the high negative pressure levels (roughly 200 millibars less than the ambient atmospheric pressure) is used to aspirate transfer liquid 24 into the microdispensers 212. Once the transfer liquid 24 has been aspirated into the microdispensers 212, the low negative pressure levels (roughly −15 millibars gauge) are used to supply back pressure to the transfer liquid 24 in the microdispensers 212 such that as droplets are dispensed, no additional transfer liquid 24 leaves the microdispensers 212.

System liquid 20 in the system reservoir 214 is coupled to the microdispensers 212 through a distribution tube 234 that splits into a plurality of sections 236, as shown in FIG. 7, with one section 236 connected to each microdispenser 212. Attached to each of the distribution tube sections 236 are solenoid valves 242 and flow sensors 244. The system controller 224 sends electrical signals through an electrical connection 246 to control the valves 242. A flow sensor 244 is attached to each distribution tube section 236 to determine the amount of liquid that is being aspirated into each microdispenser. The flow sensor 244 detects the flow of system liquid 20 into or out of each microdispenser 212. The flow sensors 244 are each connected to the system controller 224 through an electrical conductor 248. The electrical conductor 248 carries electrical signals from each flow sensor 244, indicating not only the amount of liquid flow, but also the pressure in each flow sensor. The flow sensors 244 are microfabricated. This is advantageous since the sensors are small and fit easily into the microvolume liquid handling system 210. An example of the flow sensors 244 is described in IEEE Proceedings, MEMS 1995, Publication No. 0-7803-2503-6, entitled, "A Differential Pressure Liquid Flow Sensor For Flow Regulation and Dosing Systems," by M. Boillat et al., hereby incorporated by reference.

The distribution tube 234, which is physically connected to the microdispensers 212, is attached to a three axis robot 238. As in the first preferred embodiment, the microdispensers are relocated to positions above different microtiter plates, wells or wafers. After the desired number of droplets has been dispensed, the robot 238 moves the microdispensers 212 to the next set of wells or wafers for further dispensing. The dispensing heads can be stationary and the robotic system can be used to locate the source and destination vessels.

It has been discovered that the ejection of individual drops of a transfer liquid in the volume range of about 100 to about 500 picoliters can be detected using the system of the present invention with a pressure detector. In order to detect dispensing of such drops, the transfer and system liquids must be substantially free of compressible gases, such as air. As used herein, the term "substantially free of compressible gas" means that the level of compressible gas, if any, is low enough to allow the detection of a drop of liquid being ejected from the system. It has been discovered that as the amount of compressible gas in the system increases, the ability to detect dispensing of the drop decreases until, at a certain level of compressible gas, the system cannot detect dispensing of a drop of the transfer liquid.

In accordance with one embodiment of the present invention, the volume from the dispensing nozzle, which holds the transfer liquid to the valve (242 in FIG. 8), is substantially free of compressible gas and is entirely enclosed. It has been discovered that in this preferred embodiment of the present invention, drops can be ejected from the closed volume until the pressure in the fluid is reduced to about −45 millibars gauge. At about −45 millibars gauge the vacuum interferes with the ejection of the drops.

In accordance with another embodiment of the present invention, the volume from the dispensing nozzle to the reservoir of system liquid is substantially free of compressible fluid (gas). It has been discovered that upon dispensing a drop of liquid, the system of this embodiment can detect a pressure change in the system liquid resulting from such drop being dispensed. The pressure change is transient. As the transfer liquid flows into the volume adjacent to the nozzle, effectively replacing the ejected drop volume, the pressure rises to the level prior to the dispensing of the drop. It has been discovered that for dispensing drops in the size range of from about 100 to about 500 picoliters, the time required for the pressure to reach the original level can be in a range of from about 5 to about 10 milliseconds. This time period can be controlled by selecting the size and confirmation of the orifice located between the volume that is adjacent to the nozzle and the reservoir. It has been determined that purging the air out of the system with a fluid (gas) that has a high solubility coefficient with respect to the system liquid has greatly reduced the residual compressible fluid (gas) in the system after priming with system liquid. Once the system is primed, keeping compressible fluids (e.g., air) out of the system is facilitated by degassing the system liquid, pressurizing the system liquid reservoir with an inert gas, utilizing low permeability tubing, and also degassing system liquid in-line. To aid in elimination of air bubbles, carbon dioxide purging can be employed as described in IEEE Proceedings, MEMS 1995, Publication No. 0-7803-2503-6, entitled "Carbon Dioxide Priming Of Micro Liquid Systems," by R. Zengerle et al.

An example of the ability of the system to dispense single drops is provided in parent application Ser. No. 09/056,233, U.S. Pat. No. 6,203,759, and illustrated in FIGS. 8–11.

In accordance with another aspect of the present invention, several methods have been developed to minimize the amount of transfer liquid that needs to be aspirated into the dispenser. In the system of the present invention, which is capable of monitoring the ejection of single drops, the dispensing chamber has to be free of compressible fluids (gas) in order for the drops to be ejected. This requires that the chamber from the nozzle (63 in FIG. 3) to the top of the piezoelectric transducer (60 in FIG. 3) be filled with liquid. This volume is often large in comparison to the is volume of transfer liquid to be dispensed.

In accordance with one method, the system liquid and the transfer liquid are not separated from each other by an air gap, as shown in FIG. 1. Instead, the two liquids are separated by a liquid which is immiscible with either or both the transfer liquid and the system liquid.

In accordance with another method, to minimize the required aspirate volume of transfer liquid, system liquid is used to fill the dispenser before aspiration of the transfer liquid begins. It has been discovered that, as the transfer liquid is aspirated, the system liquid mixes with the transfer liquid at the interface slowly enough to allow dispensing of a large percentage of the transfer liquid without observing a dilution of the transfer liquid with the system liquid.

In embodiments which do not require use of a separate system liquid, a single liquid can be used to serve as both the system liquid and the transfer liquid.

In accordance with a further aspect of the present invention, the pressure in the dispenser (such as in dispenser 212 of FIG. 7) decreases as a result of a reduction in the system liquid reservoir (214 in FIG. 7) pressure. The valve (242 in FIG. 7) is closed, and then the nozzle of the dispensing unit can be immersed in the transfer liquid to aspirate a small quantity of the transfer liquid into the dispenser. For example, when gauge pressure in the dispenser reaches −30 millibars, submersing the nozzle in the transfer liquid may draw a sufficient amount of liquid to increase the gauge pressure to −15 millibars. It should be noted that the dispenser does not aspirate air unless the surface tension in the nozzle is exceeded by the negative gauge pressure. In the system of the preferred embodiment using dimethyl sulfoxide, the negative gauge pressure of 45 millibars does not produce air aspiration into the nozzle.

The systems described can automatically detect when the microdispenser orifice enters into a liquid and when it is withdrawn.

A pressure-based liquid detection function has been developed for the embodiments shown in FIGS. 1 and 7. This function can be used to detect when one or more micro dispensers is immersed in or withdrawn from liquid. This determination is made based on a pressure change which occurs when the microdispensers are immersed in or withdrawn from liquid. This pressure change is measured by monitoring the pressure transducer (14 in FIG. 1) or flow sensors (244 in FIG. 7). This test is performed independently for each system microdispenser.

The liquid determination process can be divided into three distinct stages.

1. Predelay

Upon receipt of a "liquid level sense" command, the algorithm allows for a user-specified predelay to be performed. The duration of the delay allows the completion of an external event (i.e., the movement of the head to an aspiration source) to occur before the software begins to look for the pressure change of an air/liquid transition. Certain external events may result in a false positive if these events trigger a pressure change. This function allows the system to identify any spurious pressure change.

In the event that the predelay is zero, the software will begin monitoring the pressure immediately upon receipt of the "liquid level sense" command. This can also be applied in systems where the microdispensers are stationary and the robotic system moves the source, or aspiration vessel.

2. Baseline Establishment

Once the predelay has expired, a baseline pressure value is established from the average of multiple readings. This baseline pressure value will then be compared to subsequent pressure readings to determine if they differ enough to indicate an air-liquid transition.

3. Liquid Detect

The last stage is utilized to compare the established baseline pressure value with the current pressure values. The current pressure value is a rolling average. This ensures that a single spurious point will not result in an incorrect liquid detection event. During this stage, the pressure is read periodically. The oldest pressure value is then removed, the newest pressure value added, and a new average calculated. This average is then compared with the baseline which was established in the previous stage. The difference between these values is assessed via a user-specified threshold value. If the magnitude of the difference is greater than the threshold, then the algorithm will conclude that a liquid detect event has occurred and will set the liquid detected states to the control logic. The same test is performed independently for each dispenser.

The algorithm will continue to monitor the system for liquid detection events until a user-specified detection duration has expired. If no pressure transition of the specified magnitude occurs during this duration, the software will notify the control logic that no air-liquid transition has occurred for that particular dispenser.

The user-specified threshold value, in units of millibar, is used to refine the liquid detection process. If true air-liquid transitions are occurring, but are not being identified, then the threshold value can be decreased, thus enhancing detection sensitivity. If false liquid-detection determinations are being made as a result of random pressure fluctuations, the threshold value can be increased, thus diminishing detection sensitivity. The pressure threshold has a positive or negative value associated with it, thus enabling the user to activate the liquid detection function when the microdispensers are either immersed in or withdrawn from liquid.

Dispensing Drops of Liquid Onto a Porous Site

It has been discovered that liquid can be aspirated and small drops of liquid can be accurately dispensed onto porous sites of a wafer, forming uniform spots that are only slightly larger than the diameter of the drops. The drops of the liquid can range of from about 5 to about 500 picoliters. Depending on the application, a single drop or plurality of drops can be dispensed onto a single site. The wafer can contain distinctly defined porous sites, or its entire surface can be porous. The pores of the site should be smaller than the diameter of the drop, preferably about 10 to about 10,000 times smaller than the diameter of the drop. The drops are ejected from an outlet, which is separated from the reaction site by a distance larger than the diameter of the drop being dispensed. Since the drop does not touch the surface of the wafer prior to being dispensed, the combined properties of the liquid and the surface of the wafer do not affect the size of the drop. Upon coming into contact with the porous site, the drop forms a spot which is only slightly larger than the diameter of the drop (generally less than about 20% larger). Since the drops can be accurately deposited onto specific sites of the wafer and they form spots that are uniform and nearly the same size as the diameter of the drop, the sites can be closely spaced on a wafer.

Figure 4:
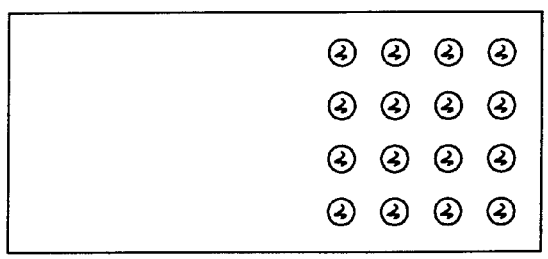
FIG. 4 is a plan view of a porous wafer on which drops have been deposited.
Figure 5:
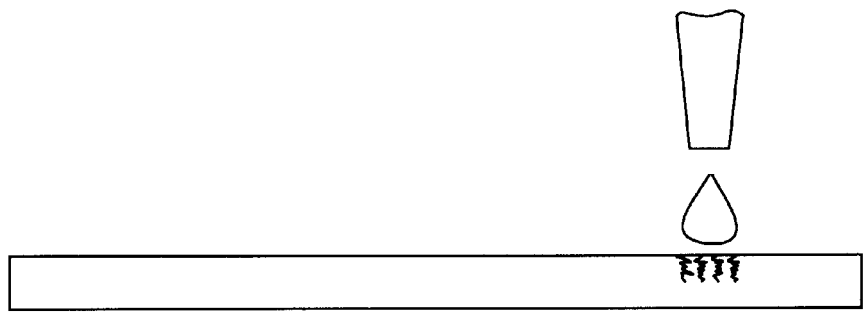
FIG. 5 is a side elevational view, partially in cross section, showing a single drop of liquid being ejected onto the reaction site of a wafer in accordance with the present invention.
Figure 6:
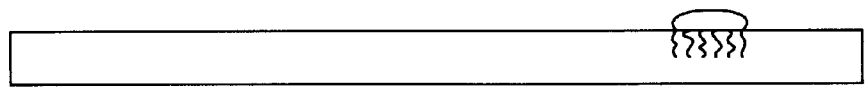
FIG. 6 is a cross sectional view of a drop of liquid penetrating the porous reaction site of a wafer.
Figure 8:
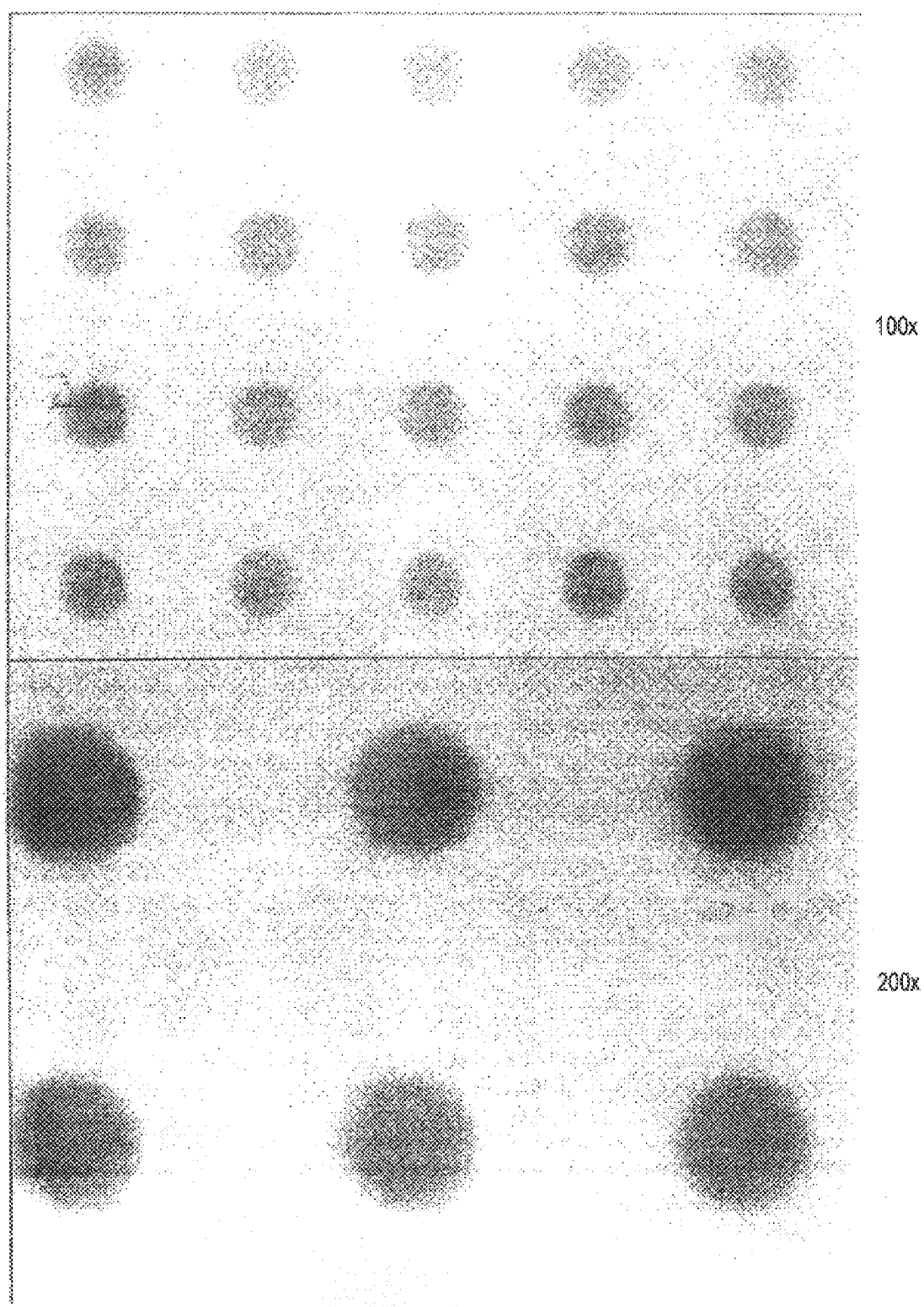
FIG. 8 shows a plurality of liquid droplets deposited onto a porous substrate in accordance with the present invention.
Figure 9:
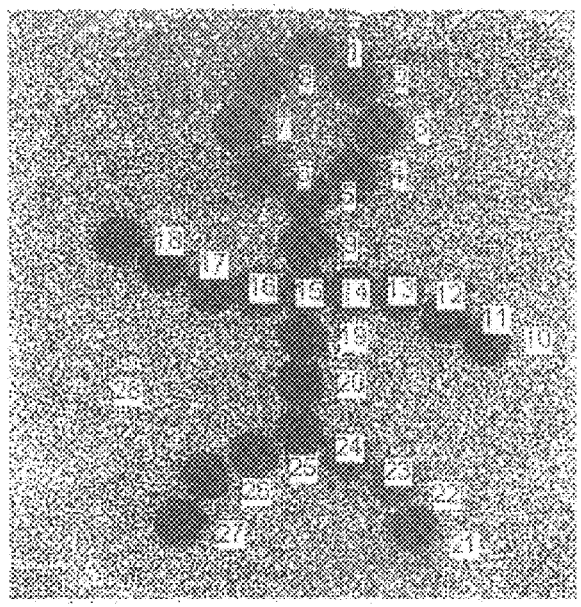
FIG. 9 shows droplets deposited on the Anapore membrane in accordance with the present invention.

The process of depositing droplets on porous substrates is generally illustrated in FIGS. 4–6. FIG. 4 illustrates the pattern of spots on a porous substrate, which provides a plurality of reaction sites. The sharply defined spots permit many reaction sites to be used for a unit area without cross-contamination of the liquids deposited. Actual results are shown in FIGS. 8–9 and discussed in Examples 1 and 2 below.

FIG. 5 illustrates a single drop being expelled from a microdispenser tip onto a porous substrate. The narrow pores extend normal to the plate of the surface so that the liquid droplet can be absorbed without spreading. Typically, the distances between the tip of the microdispenser and the wafer will be about 0.5 to 2 mm.

FIG. 6 illustrates the absorption of a drop into the porous substrate.

The dispensing of single, uniform drops in the sub-nanoliter range drop can be detected, quantified, and verified in real time. The system of the present invention is capable of automatically sensing liquid surfaces, aspirating liquid to be transferred, and then dispensing small quantities of liquid with high accuracy, speed and precision. The system of the present invention is pulsed at high frequency to prevent or eliminate clogging. Immiscible liquids between the transfer liquid and the system liquid can be used to reduce the required amount of transfer liquid needed for dispensing.

EXAMPLES

The following examples further illustrate the present invention and are not intended to limit the scope of the present invention in any manner.

Example 1

The commercial version of the dispenser described in the present application, marketed under the trademark BioChip Arrayer™, was used to deposit liquid drops onto an Anapore membrane marketed by Whatman International Ltd. The drops ejected by the BioChip Arrayer were about 85 microns and included fluorescent material.

Figure 10:
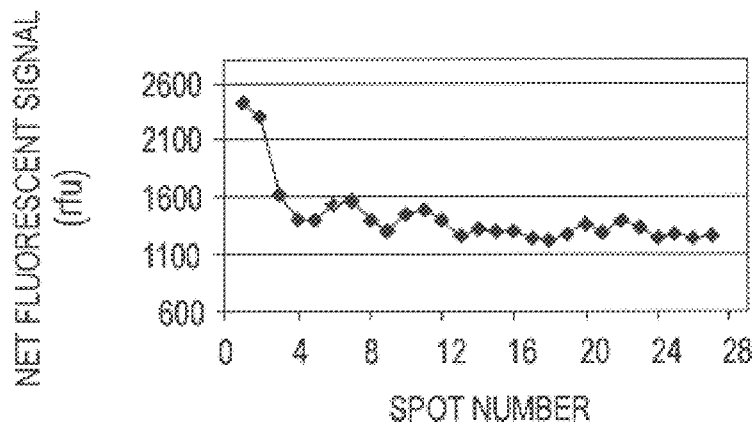
FIG. 10 is a graph of fluorescent signal from the drops deposited on the Anapore membrane as shown in FIG. 9.

Twenty-seven drops were deposited as shown in FIG. 9. The fluorescence of the drops was compared and the results are shown in FIG. 10.

As shown in FIG. 9, the spots of the 27 drops were uniform with respect to each other. As shown in FIG. 10, the fluorescence emitted from the spots was generally uniform. The fluorescent signal was significantly higher only on the first 2 of the 27 spots.

Example 2

BioChip Arrayer™ was used to deposit a plurality of drops of liquid onto an Anapore membrane. The drops contained fluorescent material and were about 85 microns in size. The resulting spots on the Anapore membrane are shown in FIG. 8, at 100× and 200×magnification. As shown in FIG. 8, the spots were uniform in size, measuring approximately 107 microns in diameter.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the claimed invention, which is set forth in the following claims.

What is claimed is:

1. A system for aspirating and ejecting drops of a transfer liquid onto a site of a wafer, said system comprising:
    said wafer containing at least one said site, each said site being porous and having pores about 10 to about 10,000 times smaller than the diameter of the drops;
    an enclosed space for holding a system liquid,
    a dispensing tube communicating with said enclosed space, said tube having an outlet, said outlet facing said site, said outlet being separated from said site by a distance greater than the diameter of said drops;
    a means for supplying a system liquid into said tube and for withdrawing from said tube said system liquid to aspirate said transfer liquid into said tube; and
    constricting means constricting the volume of said tube so as to eject drops of said transfer liquid onto said site, said tube and said constricting means adapted to produce drops in the range of from about 5 to about 500 picoliters.

2. The system of claim 1, wherein the entire surface of said wafer is porous.

3. The system of claim 1, wherein the wafer is a porous membrane.

4. The system of claim 1, wherein the transfer liquid comprises biological or chemical reactants.

5. The system of claim 1, wherein said tube and said constricting means is adapted to produce drops having a diameter of from about 10 to about 100 microns.

6. The system of claim 1, wherein said constricting means comprises a piezoelectric element.

7. The system of claim 1, wherein the distance between said outlet and said site is in the range of from about 0.5 to 2 mm.

8. The system of claim 1, wherein said system liquid comprises water.

* * * * *